United States Patent
Hosokawa

(10) Patent No.: US 6,946,279 B2
(45) Date of Patent: Sep. 20, 2005

(54) THROMBIN DERIVATIVES AND PROCESS FOR PRODUCING THE SAME, ANHYDROTHROMBIN DERIVATIVES AND PROCESS FOR PRODUCING THE SAME, PLATELET AGGLUTINATION-INDUCING COMPOSITIONS, METHOD OF INDUCING PLATELET AGGLUTINATION, CLINICAL TEST REAGENTS, CLINICAL TEST METHOD, THROMBOSIS INHIBITORS, ADSORBENT AND PROCESS FOR PRODUCING THE SAME

(75) Inventor: Kazuya Hosokawa, Kanagawa (JP)

(73) Assignees: Fujimori Kogyo Co., Ltd., Tokyo (JP); Chisso Corporation, Osaka (JP)

(*) Notice: Subject to any disclaimer, the term of this patent is extended or adjusted under 35 U.S.C. 154(b) by 0 days.

(21) Appl. No.: 10/472,237
(22) PCT Filed: Mar. 19, 2002
(86) PCT No.: PCT/JP02/02594
§ 371 (c)(1),
(2), (4) Date: Nov. 21, 2003
(87) PCT Pub. No.: WO02/077031
PCT Pub. Date: Oct. 3, 2002

(65) Prior Publication Data
US 2004/0096953 A1 May 20, 2004

(30) Foreign Application Priority Data
Mar. 19, 2001 (JP) .................................... 2001-079469

(51) Int. Cl.$^7$ .................... A61K 38/48; A61K 35/14; C12N 9/74; C07K 1/00; C07K 14/00
(52) U.S. Cl. .................... 435/214; 424/94.6; 530/383
(58) Field of Search .................... 435/214; 210/635; 530/387.1, 389.3, 383; 424/94.64

(56) References Cited

U.S. PATENT DOCUMENTS 5,939,304 A  *  8/1999  Suzuki et al. ................ 435/214

FOREIGN PATENT DOCUMENTS

EP            611774          8/1994

(Continued)

OTHER PUBLICATIONS

Ternisien, C. et al., Effect of phosphopyridoxyylation on thrombin interaction with platelet glycoprotein 1b, Apr. 1991, Blood coagulation and Fibrinolysis, vol. 2, pp. 521–528.*

(Continued)

Primary Examiner—Robert A. Wax
Assistant Examiner—Robert B. Mondesi
(74) Attorney, Agent, or Firm—Wenderoth, Lind & Ponack, L.L.P.

(57) ABSTRACT

A thrombin derivative having a lowered fibrinogen activity, a process for producing thereof, an anhydrothrombin derivative having a lowered fibrinogen activity, and a process for producing thereof are provided. This invention is to provide a thrombin derivative formed by modifying carboxyl group (s) of the thrombin and an anhydrothrombin derivative formed by modifying carboxyl group(s) of the anhydrothrombin. The thrombin derivative can be utilized as a composition for inducing platelet aggregation and further as a reagent of specific aggregation for clinical testing and the like. By affinity chromatography using carboxyl group(s) bound with anhydrothrombin as a ligand, it is made possible to carry out necessary purification with high selectivity relative to the blood coagulation factor VIII. Further, the anhydrothrombin derivative which results from modifying carboxyl group(s) of anhydrothrombin produces sufficient antithrombogenic effects at a smaller amount as compared with the previous anhydrothrombin and, therefore, can be utilized as an agent for inhibiting the thrombogenesis.

31 Claims, 6 Drawing Sheets

FOREIGN PATENT DOCUMENTS

| | | |
|---|---|---|
| EP | 615978 | 9/1994 |
| EP | 882789 | 12/1998 |
| EP | 1 195 163 | 4/2002 |

OTHER PUBLICATIONS

Vivien W.F. Chan et al., "Inactivation of Bovine Thrombin By Water–Soluble Carbodiimides: The Essential Carboxyl Group Has a PKA of 5.51", Biochemical and Biophysical Research Communications, vol. 151, No. 2, pp. 709–716, XP001194500, ISSN: 0006–291X, 1988.

Tsugikazu Tomono et al., "Preparation of Anhydro–Thrombin and Its Interaction With Plasma Antithrombin III", Acta Haematologica, S. Karger, Basel, Switzerland, vol. 49, No. 4, pp. 969–979, 1986, XP002916381, ISSN: 0001–5792.

Kazuya Hosokawa et al., "Preparation of anhydrothrombin and characterization of its interaction with natural thrombin substrates", Biochem. J., 354, pp. 309–313, 2001, and abstract thereof.

Abstract of Yoshihiko Sakurai et al., "A Novel Antithrombotic, Chemically–Modified Anhydrothrombin Inhibits Factor VIII–Mediated Intrinsic Tenase and Platelet Activation", Blood, vol. 102, No. 11, Nov. 16, 2003, p. 292a, XP002288108 & 45th Annual Meeting of the American Society of Hematology, San Diego, CA, Dec. 6–9, 2003, ISSN: 0006–4971.

* cited by examiner

THROMBIN DERIVATIVES AND PROCESS FOR PRODUCING THE SAME, ANHYDROTHROMBIN DERIVATIVES AND PROCESS FOR PRODUCING THE SAME, PLATELET AGGLUTINATION-INDUCING COMPOSITIONS, METHOD OF INDUCING PLATELET AGGLUTINATION, CLINICAL TEST REAGENTS, CLINICAL TEST METHOD, THROMBOSIS INHIBITORS, ADSORBENT AND PROCESS FOR PRODUCING THE SAME

TECHNICAL FIELD

This invention relates to a thrombin derivative and a process for producing thereof, an anhydrothrombin derivative and a process for producing thereof, a platelet aggregation inducing composition using the thrombin derivative, a method for inducing platelet aggregation, a clinical testing agent and a method for the clinical test, an antithrombotic agent using the anhydrothrombin derivative, an adsorbent and a process for producing thereof, and a process for producing a purified blood coagulation factor VIII by the use of the adsorbent.

BACKGROUND ART

In recent years, as means for synthesizing a substance for preventing thrombogenesis, a method which comprises causing the activated blood coagulation factor which is a serine protease to react with such an inhibitor as phenylmethylsulfonyl fluoride (PMSF) thereby converting active site serine into dehydroalanine and consequently eliminating the serine protease activity but retaining the binding ability with thrombin substrates (designated as "anhydridization") disclosed in the official gazette of JP-A-11-49800 and a method which eliminates the serine protease activity by the manipulation of gene recombination have been developed. The anhydrothrombin which is obtained by treating thrombin by the use of such a method inhibits interactions between activated blood coagulation factors and substrates competitively, and is expected to be utilized as a ligand for an adsorbent of thrombin substrates (such as, for example, an activated blood coagulation factor and fibrinogen) and as an inhibitor against thrombogenesis.

However, since serine protease activity of anhydrothrombin was eliminated by only the chemical treatment or the manipulation of gene recombination and its fundamental binding ability with substrates is not different from untreated thrombin, it has been difficult to absorb and to recover blood coagulation factor VIII selectively from such a liquid as plasma, which is a mixture of several thrombin substrates (such as blood coagulation factors V, VIII, XI, and XIII, fibrinogen, and Protein C). Further, the anhydrothrombin has found only limited utility because it is required to be used in an unduly large amount for the purpose of showing the same antithrombogenetic effect as the antithrombotic agent as mentioned above, though it indeed can function as an antithrombotic agent.

In diagnosis of abnormality of platelet functions, determination of ability of platelet aggregation is an essential requirement and thrombin is used for the determination as a substance that induces platelet aggregation. However, since thrombin activates fibrinogen as well as induces platelet aggregation, it has been a problem that fibrin clot exerts an adverse effect on the determination of the ability of platelet aggregation.

Concerning the thrombin which constitutes an activated blood coagulation factor or the anhydrothrombin which results from anhydridizing the thrombin, this invention has an object of providing a thrombin or anhydrothrombin derivative having an improved selectivity thereof for a thrombin substrate (blood coagulation factor VIII) by the modification using a chemical or genetic manipulation, a substance for inducing aggregation of blood platelets and a clinical testing agent containing the thrombin derivative as a component, an adsorbent using the anhydrothrombin as a ligand, and an antithrombotic agent having an improved antithrombotic ability thereof constituting the anhydrothrombin derivative as a main component.

DISCLOSURE OF THE INVENTION

The present inventor, after going through diligent studies concerning thrombin, has found that a thrombin derivative which results from modifying carboxyl group(s) of thrombin is capable of selectively decreasing the affinity for fibrinogen among thrombin substrates, namely specifically activating blood platelets exclusively by inhibiting the conversion of fibrinogen to fibrin.

This inventor, after going through diligent studies further concerning anhydrothrombin, has also acquired a knowledge that an anhydrothrombin derivative which results from modifying carboxyl group(s) of anhydrothrombin has improved specific selectivity for the blood coagulation factor VIII relatively, and consequently has improved antithrombotic ability. This invention has been perfected on the basis of the knowledge.

This invention is composed of the following items (1)–(14).

(1) A thrombin derivative formed by modifying carboxyl group(s) of thrombin.

(2) An anhydrothrombin derivative formed by modifying carboxyl group(s) of anhydrothrombin.

(3) A process for producing the thrombin derivative, characterized by modifying carboxyl group(s) of thrombin.

(4) A process for producing the anhydrothrombin, characterized by modifying carboxyl group(s) of anhydrothrombin.

(5) A composition for inducing aggregation of blood platelets, comprising the thrombin derivative set forth in the item (1) above.

(6) A method for inducing aggregation of blood platelets, characterized by using the thrombin derivative set forth in the item (1) above.

(7) A clinical testing agent, characterized by containing the thrombin derivative set forth in the item (1) above.

(8) A method for a clinical test, characterized by using the thrombin derivative set forth in the item (1) above.

(9) An antithrombotic agent, characterized by comprising the anhydrothrombin derivative set forth in the item (2) above.

(10) An adsorbent formed by combining anhydrothrombin with water-insoluble carrier, characterized by the combination being effected by the reaction of carboxyl group(s) of anhydrothrombin with functional group(s) of the water-insoluble carrier.

(11) An adsorbent formed by combining anhydrothrombin having introduced therein amino group(s) by the combination of amino group(s) of a compound having two or more amino groups and carboxyl group(s) of the anhydrothrombin with water-insoluble carrier, characterized by the combination being carried out by the reaction of the amino group(s) of anhydrothrombin introduced the amino group(s) of the water-insoluble carrier.

(12) A process for producing an adsorbent formed by the combination of anhydrothrombin and water-insoluble carrier, which method is characterized by reacting carboxyl group(s) of anhydrothrombin with the functional group(s) of the water-insoluble carrier.

(13) A process for producing an adsorbent formed by the combination of anhydrothrombin and water-insoluble carrier, which method is characterized by causing the amino group(s) introduced into the anhydrothrombin by the combination of the amino group of a compound having two or more amino groups and carboxyl group(s) of the anhydrothrombin, to react with the functional group(s) of water-insoluble carrier.

(14) A process for producing purified blood coagulation factor VIII, characterized by using the adsorbent set forth in the item (10) or (11) above.

BEST MODE OF EMBODYING THE INVENTION

Figure 1:
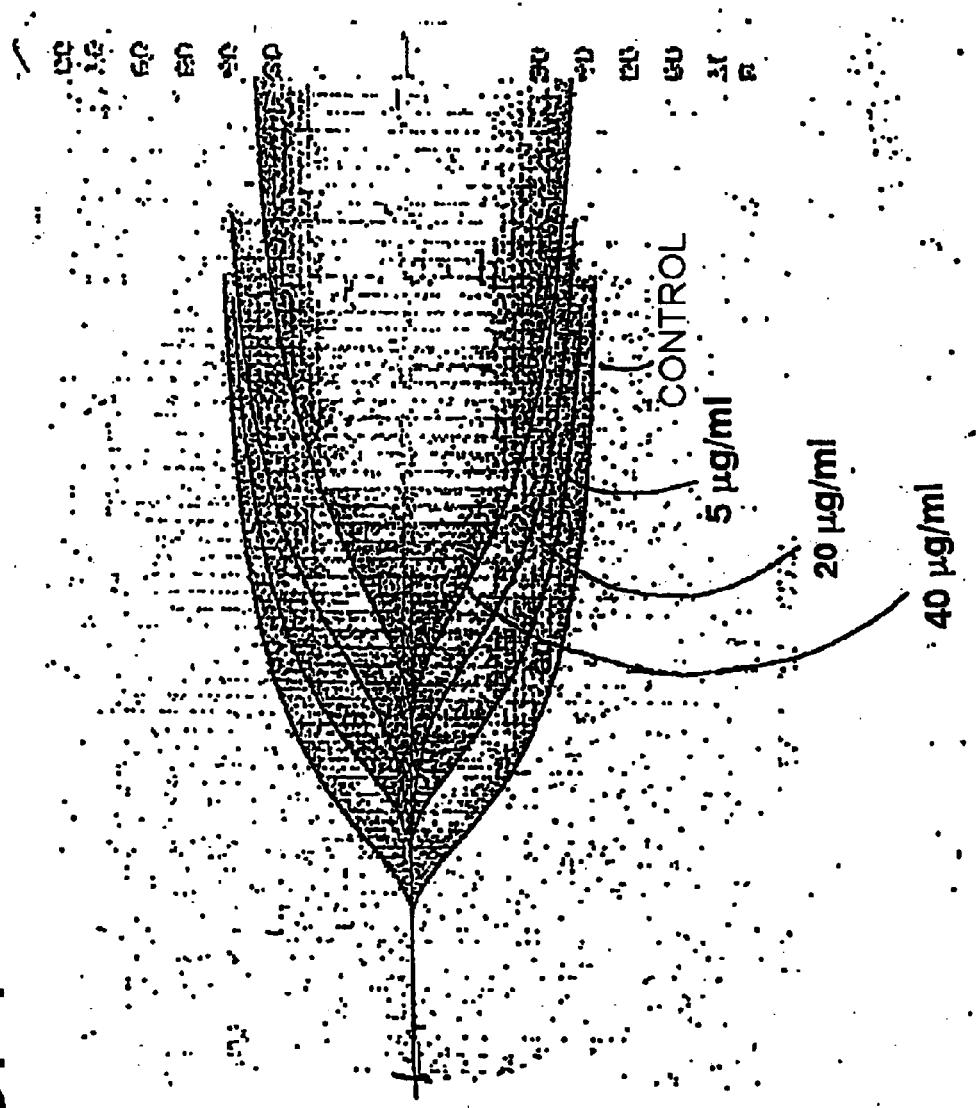
FIG. 1 is a thrombelastogram (TEG) obtained from a sample of whole blood.

Now, this invention will be described in detail below.

In the first aspect, this invention provides a thrombin derivative or an anhydrothombin derivative in which carboxyl group(s) of thrombin or anhydrothrombin are modified.

The process for producing the anhydrothrombin which constitutes the object for modification contemplated by this invention does not need to be particularly restricted. As typical examples of the anhydrothrombin, anhydrothrombin which is obtained, as disclosed in the official gazette of JP-A-11-49800, by causing the site of serine active residue of serine protease to react with such an inhibitor as PMSF and then subjecting the product of this reaction to an alkali treatment at pH of 11 more thereby carrying out anhydridization and anhydrothrombin which is obtained by a method which substitutes the active serine residue of thrombin for alanine by the technique of gene recombination, for example, thereby eliminating the enzyme activity may be cited.

The method for purifying anhydrothrombin does not need to be particularly restricted but may be selected from the heretofore known methods which are available for purification and separation. Specifically, a method which comprises passing the solution of anhydrothrombin through an affinity chromatography column equilibrated by the use of a buffer adjusted to a pH in the range of 4–10 (the buffer used during the reaction of anhydridization of serine protease may be utilized in the unmodified form) thereby carrying out selective adsorption of the anhydrothrombin on the chromatography carrier and washing the resultant adsorbate thereby removing impurities therefrom may be cited as a typical example.

Subsequently, for the purpose of desorbing the anhydrothrombin bound to the affinity chromatography carrier, a solution of a serine protease inhibitor or a solution of a substance having at least one member selected from a group of amidino group, guanidyl group, phenyl group, long-chain alkyl group, and arginine residue is adjusted to a pH in the range of 4–10 and passed through the affinity column thereby eluting the target substance from the column. By removing desorbed components by a technique of dialysis, ultrafiltration, or gel permeation, the anhydrothrombin can be obtained with high purity.

As typical examples of the serine protease inhibitor which can be utilized for the purification of the anhydrothrombin in this invention, various sulfonyl fluorides such as phenylmethylsulfonyl fluoride (PMSF), 2-phenylethane-1-sulfonyl fluoride, methane sulfonyl fluoride, and p-toluene sulfonyl (tosyl) fluoride, and tosyl chloride, diisopropyl fluorophosphoric acid (DFP), 3,4-dichloroisocoumarin (3,4-DCI), L-1-chooro-3-[4-tosyl acid]-7-amino-2-heptanone-hydrochloric acid (TLC), and L-1-chloro-3-[4-tosyl acid]-4-phenyl-1-butanone (TPCK) may be cited.

The thrombin or anhydrothrombin derivative is obtained by modifying carboxyl group(s) of anhydrothrombin or thrombin obtained as described above. The term "modify" as used herein means the modification of part or the whole of carboxyl group(s) of thrombin or anhydrothrombin. The method for carrying out this modification is preferred to resort to the imide bond or amide bond. As typical examples of this method, a method which comprises combining part or the whole of carboxyl group(s) of the anhydrothrombin with an imide, a method which comprises combining part or the whole of carboxyl group(s) of the thrombin or anhydrothrombin with a substance having an amino group, and a method which comprises combining part or the whole of carboxyl group(s) of the thrombin or anhydrothrombin with a substance having an imide and amino group thereby modifying the carboxyl group may be cited. The substances having amino groups do not need to be particularly restricted but may be compounds and naturally occurring substances. They are preferred to be such that they gain in steric bulk in the proximity of a carboxyl group. The method for carrying out such a reaction may be selected from among the heretofore known methods.

The imide which is used as described above does not need to be particularly restricted. Preferably carbodimide derivatives and more preferably carbodiimide derivatives represented by the formula, $R^1N=C=NR^2$, are advantageously used. In the foregoing formula, $R^1$ and $R^2$ independently denote such chain or cyclic alkyl groups of 1–15 carbon atoms as methyl group, ethyl group, and cyclohexyl group, (2-morpholino-ethyl)-p-toluene metosulfonates, or (3-dimethylaminopropyl) hydrochlorides. In this case, $R^1$ and $R^2$ may be the same or different. As typical examples of the carbodiimide derivatives, dicyclohexyl carbodiimide (hereinafter described as "DCC") [C$_6$H$_{11}$—N=C=N—C$_6$H$_{11}$], N-ethyl-N'-(3-dimethylaminopropyl) carbodiimide-hydrochloride [CH$_3$CH$_2$—N=C=N—(CH$_2$)$_3$N$^+$H(CH$_3$)$_2$ Cl$^-$] (hereinafter described as "EDC"), and N-cyclohexyl-N'-2-(4'-methyl-morpholinium)ethyl carbodiimide-p-toluene sulfonate) (hereinafter described as "CMC") may be cited. These carbodiimide derivatives may be used either singly or in the form of a mixture of two or more members. Among carbodiimide derivatives mentioned above, used EDC and CMC which are water-soluble carbodiimides are particularly advantageously.

In this invention, the conditions for the modification of carboxyl group(s) of thrombin or anhydrothrombin with an imide are varied by the kind and quantity of a modifying substance (imide) and other conditions. They do not need to be particularly restricted but are only required to be capable of modifying carboxyl group(s) of thrombin or anhydrothrombin to a necessary degree. One preferred embodiment of modifying carboxyl group(s) of thrombin or anhydrothrombin will be described below. First, a given thrombin or anhydrothrombin is dialyzed in a buffer of a proper pH value and the resultant dialyzate and a modifying substance are added together and stirred at a temperature in the range of 0–50° C., preferably 4–25° C., particularly preferably at normal room temperature for a period in the range of 0.5–24 hours, preferably 1–7 hours. The buffer to be used in this case is only required to be arbitrarily selected from among buffers exhibiting pH in the range of 3–9, preferably 4–7. As typical examples of the buffer, PIPES buffer, phosphate buffer, carbonate buffer, bicarbonate buffer, TRIS buffer, sodium citrate-phosphate buffer, succinic acid-sodium hydroxide buffer, potassium phthalate-sodium hydroxide buffer, imidazole hydrochloride buffer, borate-buffered saline, physiological saline, and Good's buffer may be cited. The amount of the modifying substance to be added does not need to be particularly restricted but is only required to be capable of modifying carboxyl group(s) of thrombin or anhydrothrombin to a necessary degree. The modifying substance is preferred to be present in an excess relative to thrombin or anhydrothrombin. It is preferred to be present in the buffer at a concentration in the approximate range of 0.01 M–5 M, preferably 0.1–2 M.

In the present invention, it is thought that carboxyl group(s) of thrombin or anhydrothrombin is modified as by the following formula owing to the modification of a carboxyl group with an imide (a carbodiimide derivative).

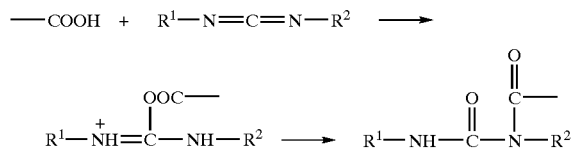

In the present invention, the modification of carboxyl group(s) of thrombin or anhydrothrombin may be carried out by using a substance which has an amino group. Owing to the modification by the use of such a substance as has an amino group, carboxyl group(s) (—COOH) of thrombin or anhydrothrombin is converted into an amide (—CO—NHR). In this case, the modification of carboxyl group(s) of the thrombin or anhydrorhombin may be carried out by using solely the substance having an amino group, it is preferred to be by using the substance having an amino group in combination with an imide. In the latter case, the substance having an amino group may be simultaneously added after the modification of carboxyl group(s) of thrombin or anhydrothrombin with an imide or during the process of the modification of carboxyl group(s) of the thrombin or anhydrothrombin with an imide.

The substance having an amino group and used in this invention does not need to be particularly restricted to a compound or a naturally occurring substance but is only required to be capable of converting carboxyl group(s) (—COOH) of thrombin or anhydrothrombin into an amide (—CO—NHR). The substance to gain in steric bulk in the proximity of the carboxyl group is used particularly advantageously. As typical examples of the substance which has an amino group, ethylene diamine, Tris hydroxyaminomethyl, hydroxyamine, ethanolamine, and ammonium chloride may be cited. Among the substances mentioned above, ethylene diamine and Tris hydroxyaminomethyl are preferable. Heretofore known methods are used for the above mentioned method. These substances having amino groups may be used either singly or in the form of a mixture of two or more members.

In the present invention, the conditions for the modification of carboxyl group(s) of thrombin or anhydrothrombin by the use of an imide and a substance having an amino group are varied by the kinds and quantities of thrombin or anhydrothrombin and a modifying substance (imide and a substance having an amino group) to be used and other conditions. They do not need to be particularly restricted but are only required to be capable of modifying carboxyl group(s) of the thrombin or anhydrothrombin to a necessary degree. Now, one preferred mode of embodying the modification of carboxyl group(s) of the thrombin or anhydrothrombin will be described below. For a start, a given thrombin or anhydrothrombin is dialyzed in a buffer of a proper pH value to eliminate impurities. The resultant dialyzate and a modifying substance are added together and stirred at a temperature in the range of 0–50° C., preferably in the range of 4–25° C., and particularly preferably at normal room temperature, for a period in the range of 0.5–24 hours, preferably in the range of 1–7 hours. The buffer which can be used in this case is only required to be selected arbitrarily from among such buffers as exhibit pH values of 3–9, from which PIPES buffer, phosphate buffer, carbonate buffer, bicarbonate buffer, TRIS buffer, sodium citrate-phosphate buffer, succinic acid-sodium hydroxide buffer, potassium phthalate-sodium hydroxide buffer, imidazole hydrochloride buffer, borate-buffered saline, physiological saline, and Good's buffer may be cited. The amounts of an imide and the substance having an amino group do not need to be particularly restricted but are only required to be capable of modifying carboxyl group(s) of thrombin or anhydrothrombin to a necessary degree. The amount of an imide to be added is preferred to allow the presence of an excess relative to thrombin or anhydrothrombin. It is properly contained in the buffer, for example, at a concentration in the range of 0.01–5 M, preferably in the range of 0.1–2 M. The amount of the substance having an amino group to be added is preferred to allow the presence of an excess relative to thrombin or anhydrothrombin. It is properly contained in the buffer, for example, at a concentration in the range of 0.1–5M, preferably in the range of 0.5–2 M.

In the present invention, it is thought that carboxyl group(s) of thrombin or anhydrothrombin is made to undergo such a modification as is represented by the following formula owing to the modification of carboxyl group(s) with an imide (carbodiimide derivative) and a substance having an amino group.

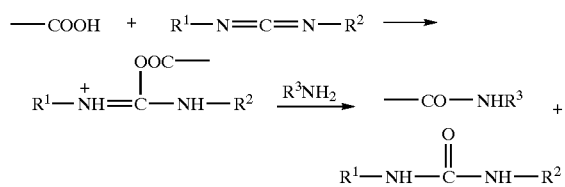

In the present invention, the thrombin derivative mentioned above is characterized by being formed by combining a part or a whole of the caraboxyl group of thrombin with an imide or by combining thrombin with an imide and a compound having an amino group thereby selectively lowering the affinity of the thrombin for fibrinogen and consequently inhibiting the conversion of fibrinogen to fibrin and specifically activating blood platelets exclusively. Thus, the thrombin derivative of this invention is useful as a substance for inducing aggregation of blood platelets and further as a clinical testing agent and particularly as a testing agent for monitoring the normality of blood platelets.

In the present invention, the anhydrothrombin derivative mentioned above is characterized by being formed by combining a part or a whole of carboxyl group(s) of anhydrothrombin with an imide or combining anhydrothrombin with an imide and a compound having an amino group thereby enabling the anhydrothrombin to acquire enhanced selective affinity for the blood coagulation factor VIII and improved antithrombogenicity owing to some sort of action or effect on blood coagulation factors including the blood coagulation factor VIII and blood platelets. Thus, the anhydrothrombin derivative of this invention is useful as an adsorbent, especially an adsorbent for a purification of the blood coagulation factor VIII, and as an antithrombotic agent, especially as a blood coagulation factor VIII-specific one.

The second aspect of the present invention resides in a substance for inducing blood platelet aggregation and a clinical testing agent both of which have the thrombin derivative as a component resulting from modifying carboxyl group(s) of thrombin. Since the thrombin derivative of this invention reduces affinity for fibrinogen due to the modification and reduces the formation of fibrin by thrombin, it is possible to induce blood platelet aggregation specifically with no influence of fibrin clot. Owing to this quality, it can be used as a reagent for the clinical test of thrombosis, for example.

The third aspect of this invention resides in providing an antithrombotic agent which contains the anhydrothrombin derivative formed by modifying carboxyl group(s) of anhydrothrombin. Clinically, numerous diseased states necessitate repression of blood coagulation and, depending on the relevant conditions, require administration of an antithrombotic agent. The antithrombotic agent contemplated by this invention proves favorable in terms of safety and cost because it derives from a physiological substance and shows antithrombotic effect at a smaller dosage as compared with the previous antithrombotic agent containing anhydrothrombin.

The forth aspect of this invention resides in providing an adsorbent which is formed by combining the carboxyl group(s) of anhydrothrombin and the functional group on a water-insoluble carrier.

Though the carrier to be used in this invention may be arbitrarily selected from among the heretofore known carriers, the carrier of a water-insoluble type can be used advantageously. The term "water-insoluble carrier" as used in the present specification means either a carrier which has a water-insoluble component or a carrier which is formed of a substance obtained by insolubilizing a water-soluble substance by a treatment such as, for example, a cross-linking reaction. As typical examples of the water-insoluble carrier, cross-linked agarose, cellulose, chitosan, and polyacrylamide may be cited. Among other water-insoluble carriers mentioned above, cellulose and cross-linked agarose are used preferably as the carrier. The shape of the water-insoluble carrier does not need to be particularly restricted but may be arbitrarily selected from among the heretofore known shapes. As typical examples of the shape, spherical particles, hollow fibers, and membranes may be cited.

In this invention, when the water-insoluble carrier has the shape of spherical particles, the spherical particles are preferred to have high sphericalness, though they do not need to be accurate spheres. Specifically, the spherical particles properly have sphericalness of 0.9 or more, and preferably 0.95 or more. The term "sphericalness" as used in the present specification means the ratio of the largest diameter (major axis) to the smallest diameter (minor axis) of particles (minor axis/major axis). Thus, the sphericalness increases in proportion as the value thereof approaches 1.0.

In this invention, when the water-insoluble carrier has the shape of spheres, it is preferred to be spherical cellulose. By using the spherical cellulose as the water-insoluble carrier, the anhydrothrombin which is a ligand is enabled to be easily immobilized and the activated blood coagulation factor VIII adsorbent containing the anhydrothrombin as a ligand is enabled to gain in biocompatibility and strength. The adsorbent of this invention, therefore, is useful as an adsorbent for the activated and/or non-activated blood coagulation factor VIII. The term "biocompatibility" as used herein means the fact that the carrier releases no harmful substances to the living body when used as a absorbent carrier in the purification process.

In the present invention, when the water-insoluble carrier has the shape of hollow fibers, this statement means that the carrier is formed of fibers containing therein continuous or discontinuous cavities. This carrier is enabled to form cavities therein by adding a foaming agent to the spinning solution or by using a special spinneret.

Further, in the present invention, when the water-insoluble carrier has the shape of membranes, as the water-insoluble carrier, a membrane filter having a porous texture and a fixed range of exclusion limit such as a commercially available membrane filter may be cited.

In the present invention, the method for immobilizing carboxyl group(s) of anhydrothrombin on the water-insoluble carrier may be arbitrarily selected from among the heretofore known methods. As typical examples of the method, a method which comprises using EDC or CMC which is a water-soluble carbodiimide and combining it with the amino group on the water-insosluble carrier and a method which comprises combining carboxyl group(s) of anhydrothrombin with EDC or CMC, subsequently condensing the resultant product of combination with a compound which has a plurality of amino groups such as ethylene diamine, and thereafter combining the introduced amino group with an N-hydroxysuccinimide (hereinafter referred to as "NHS") on the water-insoluble carrier may be cited. As regards the method of the combination, the combination by the use of an NHS combining carrier is particularly preferable because it does not effect on the amino group of the anhydrothrombin which is a ligand during the blocking of the excess active group.

The spacer to be inserted between the water-insoluble carrier and the ligand does not need to be particularly restricted but may be properly selected from among the heretofore known compounds which contain epoxy group, formyl group, etc. and also have appropriate lengths.

The fifth aspect of this invention resides in providing a method for the production of an activated blood coagulation factor VIII by the use of an activated coagulation factor VIII adsorbent according to the fourth aspect of this invention. By using this method, an activated blood coagulation factor VIII can be selectively adsorbed without a substantial adsorption of a fibrinogen and an activated blood coagulation factor V which are other thrombin substrates. The possibility of a contamination of a substance which is an immunogen, a foreign protein, and a virus is significantly repressed.

The method of this invention for the production of the activated blood coagulation factor VIII comprises packing a column with the activated coagulation factor VIII adsorbent, using the column for selectively adsorbing the activated blood coagulation factor VIII from the blood plasma component containing other blood coagulation factors or the solution such as of blood plasma including foreign protein or virus as an extraneous matter, and attaining recovery or removal to a high degree.

EXAMPLES

Now, the present invention will be described more specifically below with reference to working examples.

Example 1

Synthesis of Anhydrothrombin

Sixty (60) mg of thrombin originating in human blood plasma was dissolved in 100 ml of a 50 mM phosphate buffer (pH 6.5) containing 0.15 M of NaCl and 0.1% of PEG. To the solution, 100 µl of a 7% PMS methanol solution was added three times 30 minutes apart. While the reaction was proceeding, the solution was kept at a temperature of 25° C. After the reaction, the thrombin activity was not more than 1%. The PMS-thrombin solution was poured into a Sephadex G-25 column (made by Pharmacia Corp) equilibrated in advance with a 10 mM phosphate buffer (pH 6.5) containing 0.1 M of NaCl and 0.1% of PEG to change of the buffer.

The solution mentioned above adjusted to 4° C. and 120 ml and 1N NaOH added thereto till a final concentration of 0.05 M were left reacting for 12 minutes. The resultant solution and 60 ml of a 3N NaCl added thereto and 150 ml of glycerin subsequently added thereto were stirred together. The solution was dialyzed in a 10 mM phosphate buffer (pH 6.5) containing 10 times its volume of 1M NaCl and 0.1% PEG and then dialyzed again in a 10 mM phosphate buffer solution (pH 6.5) containing 0.1 M NaCl and 0.1% PEG.

Example 2

Purification of Anhydrothrombin

The anhydrothrombin solution obtained in Example 1 was concentrated to 50 ml by the use of Biomax 10 (made by Millipore Corp). The concentrated solution and 30 mg of p-amidinophenyl methane sulfonyl fluoride (APMSF) were added together to inactivate the residual activity.

The resultant solution was added to a benzamidine Seplharose column equilibrated in advance with a 5 mM phosphate buffer containing 0.1% of PEG. The solution was washed with the same buffer till the peak completed and then eluted with 0.2 M benzamidine (pH 6.5) containing 0.1M NaCl, to obtain three aliquot fractions each of 20 ml. These fractions were tested for protein content to confirm the fraction containing anhydrothrombin. This fraction was dialyzed in a 50 mM phosphate buffer (pH. 6.5) containing 0.1 M NaCl to remove the benzamidine in the fraction. The resultant solution was found to have a protein content of 30 mg (yield 50%).

Example 3

Modification of Anhydrothrombin

Thirty (30) mg of the anhydrothrombin obtained in Example 2 was dialyzed in 20 mM PIPES buffer adjusted in advance to pH 6 containing 0.5 M of NaCl. The solution obtained by the dialysis was adjusted to 30 ml and then stirred with EDC added thereto till a concentration of 20 mg/ml. They were left reacting at room temperature for three hours to obtain 30 mg of an EDC-modified anhydrothrombin as an anhydrothrombin derivative.

Example 4

Production of Anhydrothrombin-Combined Affinity Chromatography

Thirty (30) mg of the anhydrothrombin obtained in Example 2 was dialyzed in 10 ml of 20 mM PIPES buffer adjusted in advance to pH 6 containing 0.5 M NaCl and the resultant dialyzate was added to 20 ml of Aminocellulofine (made by Chisso Corp.). The solution was again adjusted to pH 6 and then left reacting with EDC added thereto till a concentration of 20 mg/ml at room temperature for six hours.

Example 5

The cellulose gel obtained in Example 4 was packed in a column and equilibrated by the use of a 50 mM PIPES buffer containing 0.1 M NaCl, pH 6.5. The solution of Confact F (made by Kaketsuken) dissolved in the same buffer was added to the equilibrated gel and the non-adsorbed peak was washed with the same buffer. The column was further washed with a 50 mM PIPES buffer containing 0.3 M NaCl, pH 6.5, to expel the fibrinogen still included therein and then washed with a 50 mM PIPES buffer containing 0.1 M NaCl and 1 M arginine hydrochloride, pH 6.5, to elute the blood coagulation factor VIII. The included fibrinogen was removed and the blood coagulation factor VIII having about 1000 u/mg of specific activity was recovered.

Example 6

A sample of whole blood having the derivative obtained in Example 3 added thereto was tested for the thromboelastogram (TEG). The result is shown in FIG. 1. The EDC-modified anhydrothrombin of this invention, as shown in FIG. 1, effected extension of the coagulation in a pattern depending on concentration.

Example 7

A sample of human blood plasma and the anhydrothrombin derivative (EDC-modified anhydrothrombin) of Example 3 were added together and tested for the activated partial thromboplastin time (APTT) (Table 1) and the prothrombin time (PT) (Table 2).

TABLE 1

| | Blood plasma coagulation time at varying concentration of addition | | |
|---|---|---|---|
| | No addition | 0.1 mg/ml | 0.2 mg/ml |
| EDC-modified anhydrothrombin | 42.5 sec | 115 sec | >180 sec |
| Anhydrothrombin | 42.5 sec | 45 sec | 50 sec |

TABLE 2

| | Blood plasma coagulation time at varying concentration of addition | | |
|---|---|---|---|
| | No addition | 0.1 mg/ml | 0.2 mg/ml |
| EDC-modified anhydrothrombin | 24 sec | 26 sec | 31 sec |
| Anhydrothrombin | 24 sec | 25 sec | 28 sec |

From the results shown in Tables 1 and 2, it is ascertained that the EDC-modified anhydrothrombin which is an anhydrothrombin derivative of this invention extended the blood plasma coagulation time in a pattern peculiar to APTT, depending on concentration. In further consideration of the fact that the APTT concerns the endogeneous coagulation and the PT concerns the exogeneous coagulation, the results suggest that the EDC-modified anhydrothrombin which is an anhydrothrombin derivative of this invention extended the coagulation time regarding the endogeneous coagulation and not the exogeneous coagulation and therefore proves useful as an antithrombotic agent. Further, the results of the above Example 5 and thefollowing Example 11 show that the anhydrothrombin derivative of this invention specifically binds to the blood coagulation factor VIII, suggesting that it is useful as an antithrombotic agent specific to the blood coagulation factor VIII.

Example 8

Four (4) mg of human thrombin was dissolved in 4 ml of a 50 mM PIPES buffer containing 0.1 M NaCl, pH 6.5. The resultant solution and 100 mg of EDC added thereto were left reacting for three hours to obtain an EDC-modified thrombin as a thrombin derivative. The substance mentioned above was tested as an inducing substance for blood platelet aggregation using a sample of human platelet rich plasma (PRP) adjusted in advance to a platelet count of 400,000/$\mu$l. The aggregation was determined by monitoring the decrease of absorbance (by the use of an aggregation meter sold under the trademark designation of ("Agritech TE-500"). To 240 $\mu$l of PRP, the EDC-modified thrombin was added as the inducing substance in two sizes, i.e. 10 $\mu$l and 100 $\mu$l. A control was performed by using 10 $\mu$M of thrombin.

Figure 2:
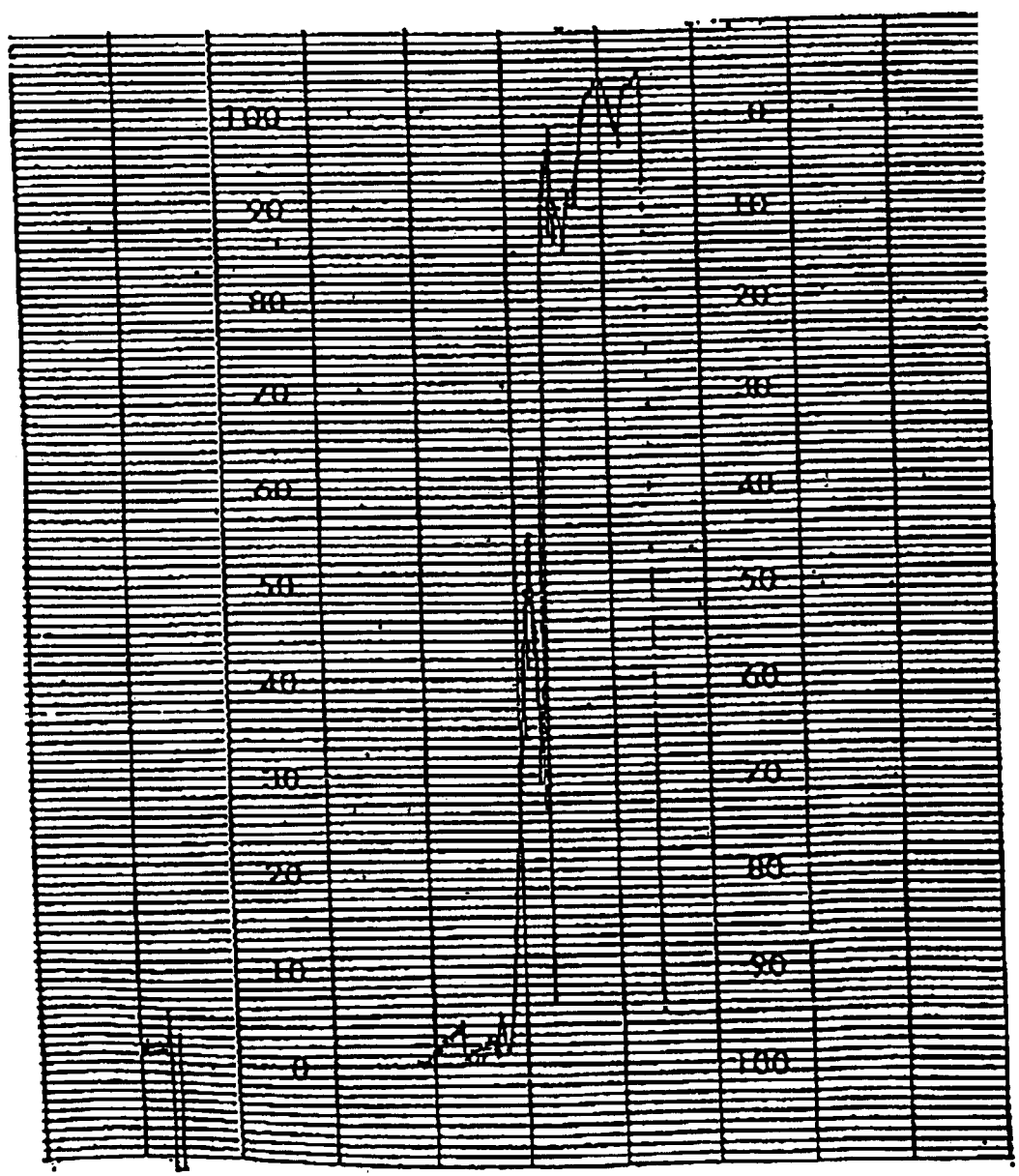
FIG. 2 is a graph showing the change of a platelet aggregation (change in the absorbance) of a sample after addition of 10 μl thrombin in Example 8.
Figure 3:
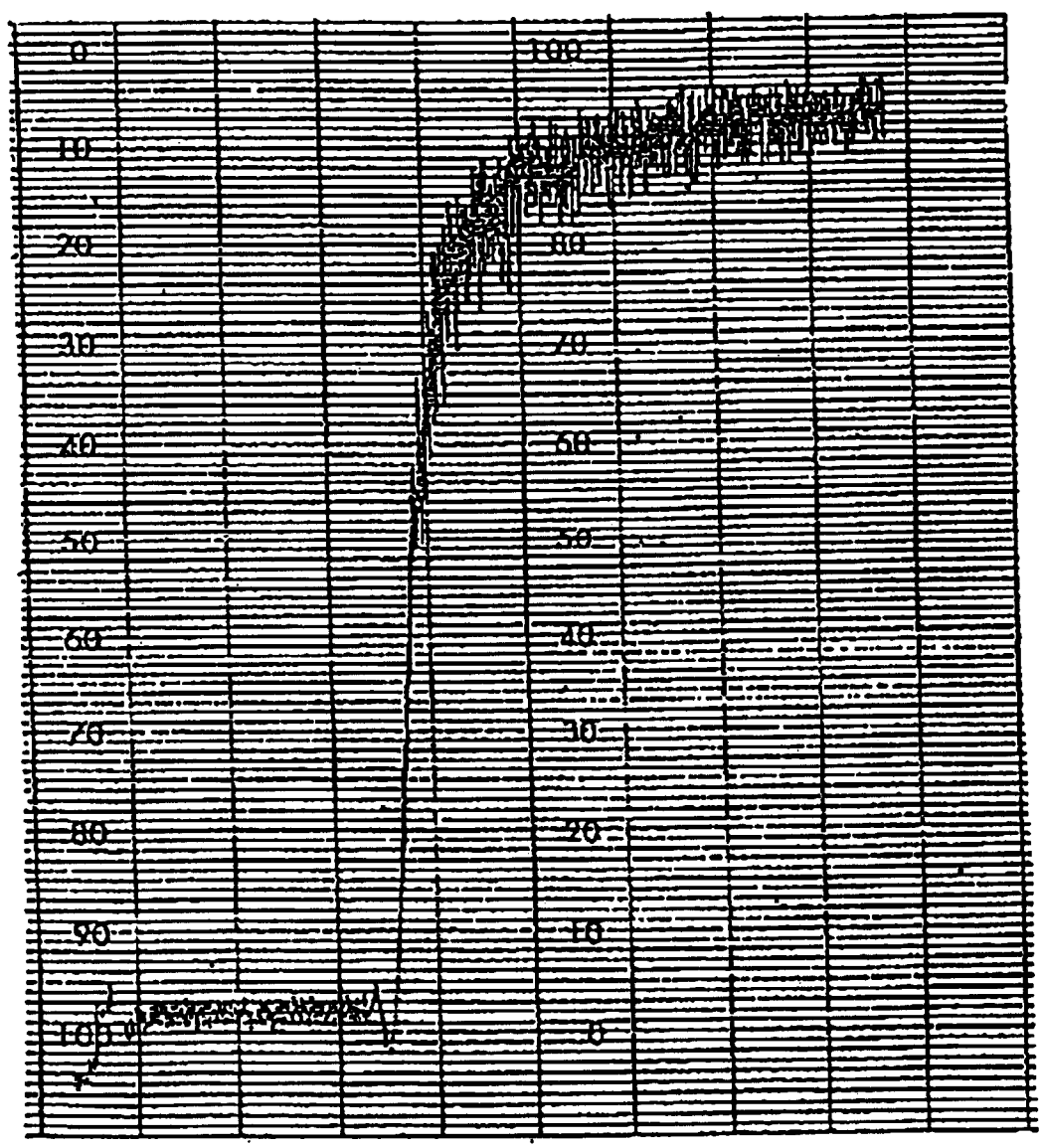
FIG. 3 is a graph showing the change of a platelet aggregation (change in the absorbance) of a sample after addition of 100 μl EDC-modified thrombin in Example 8.
Figure 4:
FIG. 4 is a graph showing the change of a platelet aggregation (change in the absorbance) of a sample after addition of 10 μl EDC-modified thrombin in Example 8.

FIG. 2, FIG. 3, and FIG. 4 are graphs showing changes of blood platelet aggregation (changes in absorbance) after the addition of 10 $\mu$l of thrombin, 100 $\mu$l of the EDC-modified thrombin, and 10 $\mu$l of the EDC-modified thrombin respectively. From FIG. 2, FIG. 3, and FIG. 4, it is noted that the use of the EDC-modified thrombin allowed the monitoring to be performed with small noise as compared with the control using thrombin.

To be more specific, the thrombin is a substance inducing thrombogenesis and has constituted one of the substances for activating blood platelets for the purpose of monitoring the normality of blood platelets. As shown in FIG. 2, however, the use of the thrombin resulted in emitting noise considerably during the course of the monitoring. This noise is thought to arise because the thrombin induces not merely the activation of blood platelets but also the transformation of fibrinogen to fibrin. For the purpose of selectively monitoring the normality of blood platelets exclusively, it is necessary to remove fibrinogen from the thrombin. In contrast, the EDC-modified thrombin which is a thrombin derivative of this invention was demonstrated to be capable of specifically activating the blood platelets exclusively with virtually no generation of noise, namely without inducing transformation of fibrinogen to fibrin, during the course of the monitoring as illustrated in FIG. 3 and FIG. 4. The monitoring of the normality of blood platelets, therefore, is not thought to necessitate removal of fibrinogen. Though the following discussion is not meant to impose any limitation on this invention, the restraint (or inhibition) effected by the thrombin derivative of this invention on the transformation of fibrinogen to fibrin is thought to occur because the modification of carboxyl group(s) of thrombin results in modifying the site of activation of fibrinogen by thrombin.

The results are thought to justify a conclusion that the thrombin derivative of this invention is useful as a substance for inducing platelet aggregation and further as a clinical testing agent, particularly as a clinical testing agent for monitoring the normality of blood platelets.

Example 9

(i) Preparation of Ethylene Diamine-Modified Thrombin

Thrombin was added to a heparin column and adsorbed thereon and the adsorbate was eluted by the use of a 1 mM PIPES buffer containing 0.5 M NaCl, pH 6.5. The resultant thrombin-containing solution (0.6 mg/ml) was mixed with a solution containing the same amount of ethylene diamine (1 M ethylene diamine-1 mM PIPES-0.5 M MnCl, pH 6.5). To the resultant mixture, EDC was added so as to give a final concentration of 20 mg/ml. Over a period of two hours after the addition of EDC, the mixture was stirred at normal room temperature to induce a reaction of condensation. After 1, 15, 30, 60, 90, and 120 minutes following the addition of carbodiimide (0 minute of reaction), portions of the mixture were collected as samples.

(ii) Clot Activity of Ethylene Diamine-Modified Thrombin to Fibrinogen

The samples collected after the elapse of 0 minute, 1 minute, 15 minutes, 30 minutes, 60 minutes, 90 minutes, and 120 minutes respectively of the aforementioned reaction and the same amounts of buffer (50 mM NaHCO$_3$ and 0.1 M NaCl, pH 8.0) were added together to stop the reaction of condensation.

The resultant samples measuring 300 $\mu$l apiece and as many portions of a fibrinogen solution (about 0.1%) measuring 1 ml apiece were respectively added and the produced mixtures were tested for the fibrinogen coagulation time at room temperature.

Figure 5A:
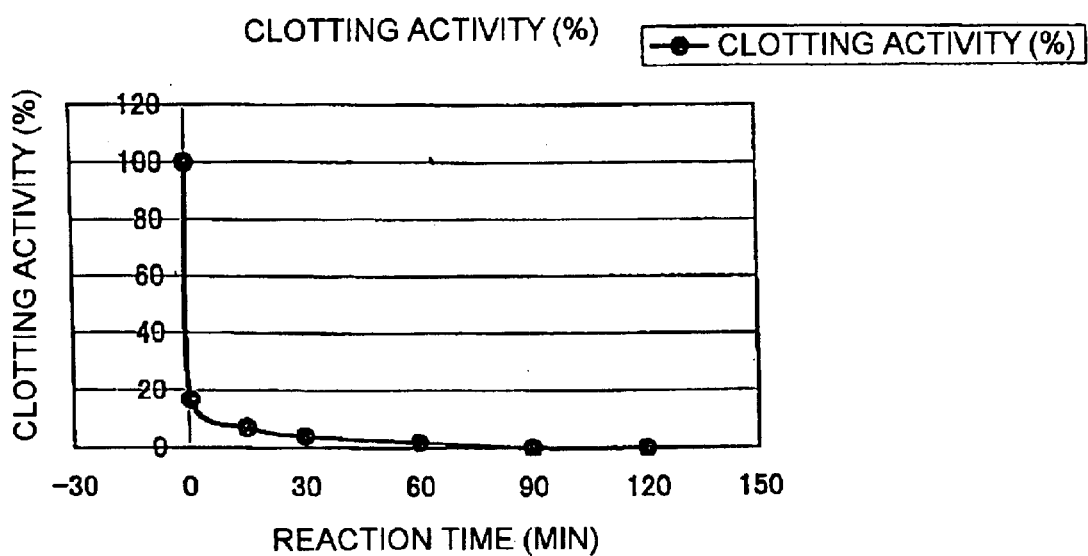
FIG. 5A is a graph showing the coagulating activity on fibrinogen by the modified thrombin obtained in Example 9 and the quantity of amino group (amine).

When the individual samples were rated for coagulation activity with the coagulation time of the sample representing the time of 0 minute of the reaction taken as 100%, their magnitudes of activity diminished and, at and after the time of 60 minutes of the reaction, nearly ceased to exist. The results are shown in FIG. 5A.

(iii) Assay of Ethylenediamine-Modified Thrombin for Amino Group Content

The samples representing the designated times of 0 minute, 1 minute, 15 minutes, 30 minutes, 60 minutes, 90 minutes, and 120 minutes of the reaction of the foregoing paragraph (i) were made to stop the reactions proceeding therein by the addition of a small amount of a strong alkali solution and were thoroughly dialyzed using a 0.5 M NaCl-50 mM NaOH solution to remove unbound ethylene diamine.

The sample solutions thus obtained, after adding first a 0.1 M $Na_2SO_3$ and then a TNBS (trinitrobenzene sulfonic acid) solution apiece, were speedily stirred and, after the elapse of 5 minutes thence, made to stop the reactions proceeding therein by the addition of a solution containing a sulfite ion.

The resultant sample solutions were tested for absorbance at 420 nm (denoted by "A420" in FIG. 5B) so as to assay the relevant samples for the amino group content.

Figure 5B:
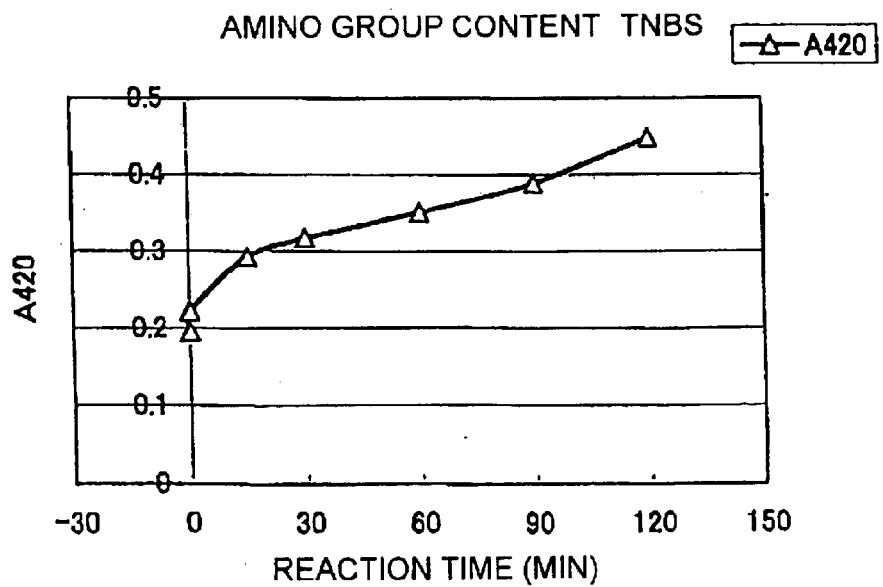
FIG. 5B is a graph showing the absorbance at 420 nm and amino group content of ethylene diamine-modified thrombin obtained in Example 9.

The results are shown in FIG. 5B. They demonstrate that the absorbance grew and the amount of the reaction of condensation of ethylene diamine onto the surface of thrombin gained in accordance as the time of the reaction of condensation elapsed. Incidentally, since aspartic acid and glutamic acid which are dicarboxylic acids were present on the surface of thrombin, the treatment (i) mentioned above induced the amino group of ethylene diamine to condense with the carboxyl group. Further, since the ethylene diamine has two amino groups, the amino group which escaped being spent by the reaction of condensation was reacted with TNBS and allowed this reaction to be assayed by the absorption at 420 nm.

It is noted from the results of Example 9 that the reaction of modification using the carbodiimide on the carboxyl group(s) of the thrombin proceeded with the elapse of time. This fact ascertains that the modification carried out by the carbodiimide on the plurality of carboxyl groups contained in the thrombin proceeded with the elapse of time and the ratio of the modification carried out by the carbodiimide on the thrombin could be increased in proportion as the time of the reaction increased. The activity of coagulation carried out by the ethylene diamine-modified thrombin on the fibrinogen was completely eliminated by the ethylene diamine-modified thrombin representing the time of 60 minutes of the reaction.

The activity of coagulation on the fibrinogen suddenly began to decline at the time of 1 minute of the reaction. It is ascertained by comparing this activity with the corresponding amino acid content found by the assay that the effect of lowering the activity of coagulation manifested on the fibrinogen was obtained aptly even when the modification by the carbodiimide was carried out on part of the thrombin.

Example 10

An EDC-modified thrombin was obtained as a thrombin derivative by dissolving 4 mg of human thrombin in 4 ml of a 50 mM PIPES buffer containing 0.1 M of NaCl, pH 6.5 and allowing the resultant solution to react with 100 mg of EDC added thereto for three hours. A sample of human platelet rich plasma (PRP) adjusted in advance to a platelet count of 400,000/μl was tested for platelet aggregation by using the substance just mentioned as an inducing substance. The aggregation was determined by monitoring the decline of the absorbance by means of an aggregation meter sold under the trademark designation of ("Agritech TE-500"). The EDC-modified thrombin as an inducing substance was added in amounts adjusted to correspond to the concentrations of 91.3 nM, 36.5 nM, 30.1 nM, 24.2 nM, 20.1 nM, and 10.1 nM relative to the PFP. For the purpose of control, a sample which the EDC-modified thrombin was not added (concentration of addition: 0 nM) was used.

Figure 6:
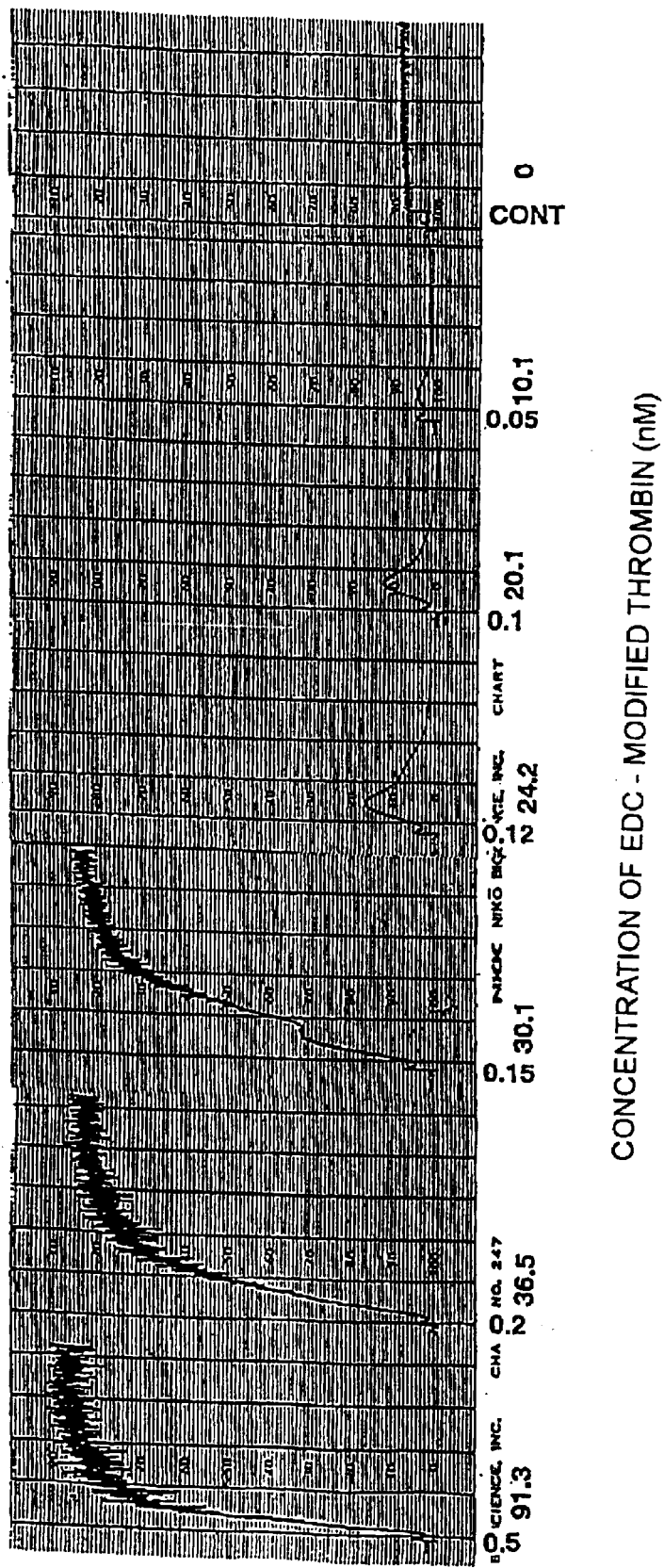
FIG. 6 is a graph showing the change of a platelet aggregation (change in the absorbance) of a sample after addition of an EDC-modified thrombin at varying concentrations in Example 10.

FIG. 6 is a graph showing changes of aggregation of blood platelets (changes of absorbance) in consequence of the addition of the EDC-modified thrombin at varying concentrations. It is ascertained by FIG. 6 that the rise of the absorbance gained in suddenness, namely the aggregation of blood platelets gained in quickness, in accordance as the concentration of addition of the EDC-modified thrombin was increased and that the EDC-modified thrombin depended on concentration in inducing the aggregation of blood platelets.

These results are thought to justify a conclusion that the thrombin derivative of this invention is useful as a substance for inducing the aggregation of blood platelet aggregation and further as a clinical testing agent, especially a testing agent for monitoring the normality of blood platelets.

Example 11

In this Example, the ethylene diamine-modified anhydrothrombin was rated for affinity for the substrate as follows.

The anhydrothrombin obtained in Example 2 was dialyzed with 1 mM PIPES buffer containing 0.5 M NaCl at pH 6.5. The anhydrothrombin-containing solution (0.6 mg/ml) consequently obtained was mixed with the same amount of an ethylene diamine-containing solution (1 M ethylene diamine, 1 mM PIPES, 0.5 M NaCl, pH 6.5). Then, to the resultant mixture, EDC was added so as to give a final concentration of 20 mg/ml. The mixture was stirred at room temperature over a period of two hours following the addition of EDC to induce a reaction of condensation. An ethylene diamine-modified anhydrothrombin was obtained by dialyzing the modified anhydrothrombin resulting from the reaction twice in a solution of 0.5 M sodium hydrogen carbonate containing 0.5 M NaCl (4° C.).

The ethylene diamine-modified anhydrothrombin obtained as described above and anhydrothrombin as the control were tested for the dissociation constant (Kd value) with fibrinogen (Fbgn), blood coagulation factor VIII (FVIII), and blood coagulation factor V (FV) through the medium of IAsys (made by Nissei Sangyo). The results are shown in Table 3.

TABLE 3

|  | FVIII | Fbgn | FV |
| --- | --- | --- | --- |
| Ethylene diamine-modified anhydrothrombin | $9 \times 10^{-9}$ | $3 \times 10^{-6}$ | $2 \times 10^{-6}$ |
| Anhydrothrombin | $1.4 \times 10^{-8}$ | $1.8 \times 10^{-8}$ | $8.5 \times 10^{-8}$ |

It is noted from Table 3 given above that the ethylene diamine-modified anhydrothrombin preserved high affinity for blood coagulation factor VIII (FVIII), while it manifested such magnitudes of affinity for fibrinogen (Fbgn) and blood coagulation factor V (FV) as were significantly lowered to the order of one of several hundred parts as compared with the affinity for FVIII. These results suggest that the ethylene diamine-modified anhydrothrombin which is an anhydrothrombin derivative of this invention was bound specifically with blood coagulation factor VIII.

INDUSTRIAL APPLICABILITY OF THE INVENTION

The thrombin derivative of this invention has lowered affinity for fibrinogen and, therefore, proves useful as a composition for inducing the blood platelet aggregation and further as a reagent of specific aggregation for clinical testing and the like. By the affinity chromatography having a carboxyl group bound with anhydrothrombin as a ligand, it is made possible to carry out necessary purification with high selectivity relative to the blood coagulation factor VIII. Further, the anhydrothrombin derivative which results from modifying carboxyl group(s) of anhydrothrombin produces sufficient antithrombogenic effects at a smaller amount as compared with the prior anhydrothrombin and, therefore, can be utilized as an agent for inhibiting the thrombogenesis.

What is claimed is:

1. An anhydrothrombin derivative formed by modifying carboxyl group(s) of anhydrothrombin.

2. An anhydrothrombin derivative according to claim 1, wherein said modification of carboxyl group(s) is carried out with an imide.

3. An anhydrothrombin derivative according to claim 2, wherein said imide is a carbodiimide derivative.

4. An anhydrothrombin derivative according to claim 3, wherein said carbodiimide derivative is at least one member selected from the group consisting of N-ethyl-N'-(3-dimethyl-aminopropyl)carbodiimidehydrochloride and N-cyclohexyl-N'-2-(4'-methylmorpholinium)-ethyl carbodiimide-p-toluene sulphonate.

5. An anhydrothrombin derivative according to claim 1, wherein said modification of carboxyl group(s) is carried out with a substance having amino group(s).

6. A process for producing an anhydrothrombin derivative set forth in claim 1, which comprises modifying carboxyl group(s) of anhydrothrombin.

7. A process for producing an anhydrothrombin derivative according to claim 6, wherein said modification of carboxyl group(s) is carried out with an imide.

8. A process for producing an anhydrothrombin derivative according to claim 7, wherein said imide is a carbodiimide derivative.

9. A process for producing an anhydrothrombin derivative according to claim 8, wherein said carbodiimide derivative is at least one member selected from the group consisting of N-ethyl-N'-(3-dimethylaminopropyl)carbodiimide hydrochloride and N-cyclohexyl-N'-2-(4'-methylmorpholinium) ethylcarbodiimide-p-toluene sulphonate.

10. A process for producing an anhydrothrombin derivative according to claim 6, wherein said modification of carboxyl group(s) is carried out with a substance having amino group(s).

11. An antithrombotic agent, comprising the anhydrothrombin derivative set forth in claim 1.

12. An adsorbent formed by combining anhydrothrombin with water-insoluble carrier, the combination being effected by the reaction of carboxyl group(s) of anhydrothrombin with functional group(s) of the water-insoluble carrier.

13. An adsorbent formed by combining anhydrothrombin having introduced therein amino group(s) by the combination of amino group(s) of a compound having two or more amino groups and carboxyl group(s) of the anhydrothrombin with water-insoluble carrier, said combination being carried out by the reaction of the amino group(s) of anhydrothrombin introduced said amino group(s) and the functional group(s) of said water-insoluble carrier.

14. An adsorbent according to claim 13, wherein said compound having two or more amino groups is an ethylene diamine.

15. An anhydrothrombin derivative according to claim 2, wherein said modification of carboxyl group(s) is carried out with a substance having amino group(s).

16. An anhydrothrombin derivative according to claim 3, wherein said modification of carboxyl group(s) is carried out with a substance having amino group(s).

17. An anhydrothrombin derivative according to claim 4, wherein said modification of carboxyl group(s) is carried out with a substance having amino group(s).

18. A process for producing an anhydrothrombin derivative set forth in claim 2, which comprises modifying carboxyl group(s) of anhydrothrombin.

19. A process for producing an anhydrothrombin derivative set forth in claim 3, which comprises modifying carboxyl group(s) of anhydrothrombin.

20. A process for producing an anhydrothrombin derivative set forth in claim 4, which comprises modifying carboxyl group(s) of anhydrothrombin.

21. A process for producing an anhydrothrombin derivative set forth in claim 5, which comprises modifying carboxyl group(s) of anhydrothrombin.

22. A process for producing an anhydrothrombin derivative according to claim 7, wherein said modification of carboxyl group(s) is carried out with a substance having amino group(s).

23. A process for producing an anhydrothrombin derivative according to claim 8, wherein said modification of carboxyl group(s) is carried out with a substance having amino group(s).

24. A process for producing an anhydrothrombin derivative according to claim 9, wherein said modification of carboxyl group(s) is carried out with a substance having amino group(s).

25. An antithrombotic agent, comprising the anhydrothrombin derivative set forth in claim 2.

26. An antithrombotic agent, comprising the anhydrothrombin derivative set forth in claim 3.

27. An antithrombotic agent, comprising the anhydrothrombin derivative set forth in claim 4.

28. An antithrombotic agent, comprising the anhydrothrombin derivative set forth in claim 5.

29. A process for producing an adsorbent formed by combination of anhydrothrombin and water-insoluble carrier, which comprises reacting carboxyl group(s) of anhydrothrombin with the functional group(s) of the water-insoluble carrier.

30. A process for producing an adsorbent formed by combination of anhydrothrombin and water-insoluble carrier, which comprises causing amino group(s) of anhydrothrombin, introduced into the anhydrothrombin by combination of an amino group of a compound having two or more amino groups and carboxyl group(s) of the anhydrothrombin, to react with functional group(s) of the water-insoluble carrier.

31. A process for producing an adsorbent formed by the combination of anhydrothrombin and water-insoluble carrier set forth in claim 29, wherein said compound having two or more amino groups is ethylene diamine.

* * * * *